United States Patent [19]
Gall

[11] Patent Number: 5,921,240
[45] Date of Patent: Jul. 13, 1999

[54] SNORE AND TEETH GRINDING PREVENTION DEVICE

[76] Inventor: Robert A. Gall, 2815 Brighton Dr., Waukesha, Wis. 53188

[21] Appl. No.: 08/862,754

[22] Filed: May 23, 1997

Related U.S. Application Data

[63] Continuation-in-part of application No. 08/802,222, Feb. 19, 1997, which is a continuation of application No. 08/558,956, Nov. 13, 1996, abandoned.

[51] Int. Cl.$^6$ .................................................... A61F 5/56
[52] U.S. Cl. ......................... 128/848; 128/859; 128/861; 602/902
[58] Field of Search ........................... 128/248, 859–862; 2/2; 602/902

[56] References Cited

U.S. PATENT DOCUMENTS

| | | | |
|---|---|---|---|
| 746,869 | 12/1903 | Moulton | 128/848 |
| 3,768,465 | 10/1973 | Helmer | 128/862 |
| 4,031,888 | 6/1977 | Walters | 128/859 |
| 5,165,423 | 11/1992 | Fowler | 128/861 |
| 5,570,702 | 11/1996 | Forman | 128/861 |

*Primary Examiner*—Michael A. Brown
*Attorney, Agent, or Firm*—Andrus, Sceales, Starke & Sawall

[57] ABSTRACT

A device is provided for preventing snoring and the grinding of teeth by a user during sleep. The device includes a generally oval plate positioned in the mouth of the user between the teeth and the lips. The oval plate includes an aperture centered therein to accommodate air flow into and out of the mouth. A tab member extends from a first side of the oval plate and through the lips to position the air passage in the flow of air into and out of the mouth when the lips are separated. The device reduces the flow of air into the mouth and hence, reduces the vibration of the uvula, which, in turn, reduces the snoring sound. The device further includes a tapered rib extending along a second side of the oval plate so as to prevent the upper teeth of a user from engaging the lower teeth of a user.

25 Claims, 3 Drawing Sheets

SNORE AND TEETH GRINDING PREVENTION DEVICE

This is a continuation-in-part of Ser. No. 08/802,222, filed Feb. 19, 1997 which is a continuation of Ser. No. 08/558,956, filed Nov. 13, 1996, now abandoned.

BACKGROUND AND SUMMARY OF THE INVENTION

This invention relates to snore and teeth grinding prevention devices, and more particularly, to a snore and teeth grinding prevention device which limits the air flow into and out of the mouth of a user in order to minimize snoring and which discourages the grinding of teeth during sleep.

The rough, harsh sound known as snoring is caused when a person breathes through their mouth during sleep so as to vibrate the uvula and/or soft palate in the interior of the mouth. In addition to the irritating snoring sound, it has been suggested that mouth breathing is unhealthy, as it contributes not only to unpleasant dry mouth syndrome, but also contributes to the development of gum diseases such as pyorrhea.

In order to combat snoring, a wide variety of snore prevention devices have been developed. Moulton U.S. Pat. No. 746,869 and Stukey U.S. Pat. No. 1,483,649 show devices which block the ingress and egress of air to the mouth. While this may prevent snoring, it is commonplace for a user who cannot mouth breath to incur difficulty sleeping. Further, the proper flow of saliva and other mouth secretions is essential to maintain the moist condition within the mouth. However, by blocking off the mouth, normal circulation of saliva and mouth secretions is prevented.

Waite U.S. Pat. No. 2,178,128 attempts to solve this problem by providing perforations in the mouthpiece to allow limited inhalation and exhalation of air by the user to permit the normal circulation of saliva and mouth secretions in the mouth. However, the anti-snoring device shown in the Waite '128 patent includes no means for separating the lips of the user, which, in turn, prevents the inhalation and exhalation of air through the perforations.

Further, it is common for a person to grind their teeth during times of stress and/or during sleep. This disorder, called bruxism, affects numerous people at one time or another.

Bruxism is directly or indirectly responsible for significant dental problems. For example, the grinding of teeth can cause the teeth to become loose. In addition, persons can grind away portions of their teeth, thereby leaving the teeth damaged or, in extreme cases, fractured.

Therefore, it is a primary object and feature of the present invention to provide a snore and teeth grinding prevention device which prevents snoring, while allowing mouth breathing by the user.

It is a further object and feature of the present invention to provide a snore and teeth grinding prevention device which permits the circulation of saliva and mouth secretions.

It is a still further object and feature of the present invention to provide a snore and teeth grinding prevention device which is simple to use and inexpensive to manufacture.

It is a still further object and feature of the present invention to provide a snore and teeth grinding prevention device which prevents the grinding of teeth during sleep.

It is a still further object and feature of the present invention to provide a snore and teeth grinding prevention device which is adaptable to fit in a variety of users.

A snore and teeth grinding prevention device is provided for preventing snoring and the grinding of teeth by a user. The snore and teeth grinding prevention device includes a generally oval plate which is received in the mouth of the user between the teeth and lips. The oval plate includes an aperture centered therein for allowing the flow of air into and out of the mouth.

A tab member extends from a first side of the oval plate immediately adjacent the aperture. When the oval plate is positioned in the mouth, the tab member protrudes through the lips so as to align the aperture behind the lower lip. If the user closes the lips, the user may breath normally through the nose. On the other hand, if a user separates the lips and attempts to breath through the mouth, the aperture controls the flow of air into and out of the mouth.

The snore and teeth grinding prevention device of the present invention also includes a rib extending along the second side of the oval plate such that when the oval plate is received within the mouth, the rib is positioned between the teeth extending from the upper gum and the teeth extending from the lower gum. The rib extends along the second side of the oval plate between the first and second ends thereof. The width of the rib increases as it extends towards the first and second ends in order to compensate for the increased width of the teeth in the back of the mouth. For example, the rib is wider at the point where the molars of the mouth engage the rib and narrower at the portion where the front teeth engage the rib.

The snore and teeth grinding prevention device may be constructed of a plastic material which is heat formable. As such, the snore prevention device may be placed in heated water or some other suitable heating method, and then molded to fit into the user's mouth. Once the snore and teeth grinding prevention device is removed from the person's mouth, it is allowed to cool and will retain its molded shape.

BRIEF DESCRIPTION OF THE PREFERRED EMBODIMENT

The drawings furnished herewith illustrate a preferred construction of the present invention in which the above advantages and features are clearly disclosed as well as others which will be readily understood from the following description of the illustrated embodiment.

DETAILED DESCRIPTION OF THE PREFERRED EMBODIMENT

Figure 1:
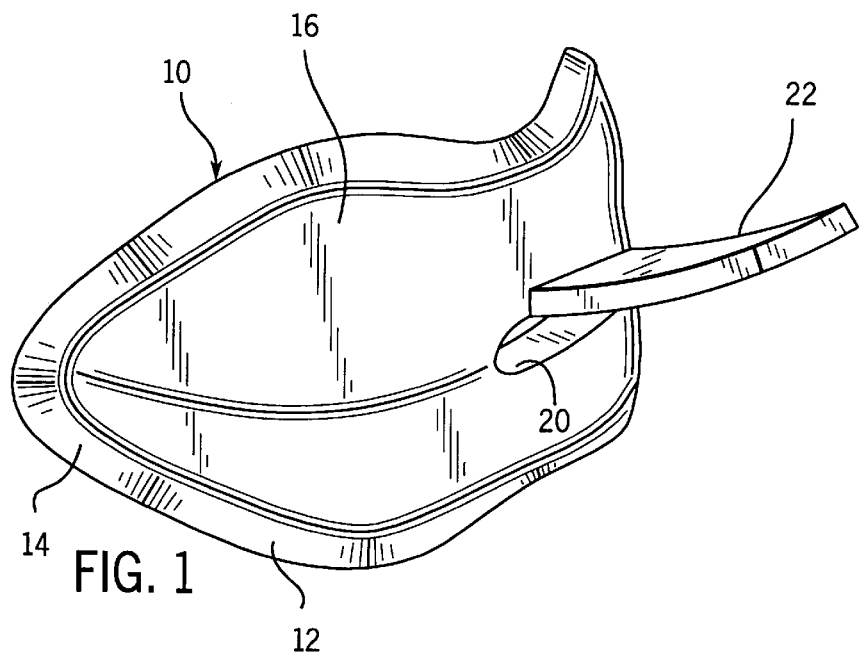
FIG. 1 is an isometric view of an anti-snore device in accordance with the present invention.

Referring to FIG. 1, the snore prevention device of the present invention is generally designated by the reference numeral 10. Snore prevention device 10 includes a generally oval plate 12 having a tapered edge 14 which prevents the cutting of the interior of a user's mouth, when the snore prevention device 10 is received therein, as hereinafter described.

Figure 4:
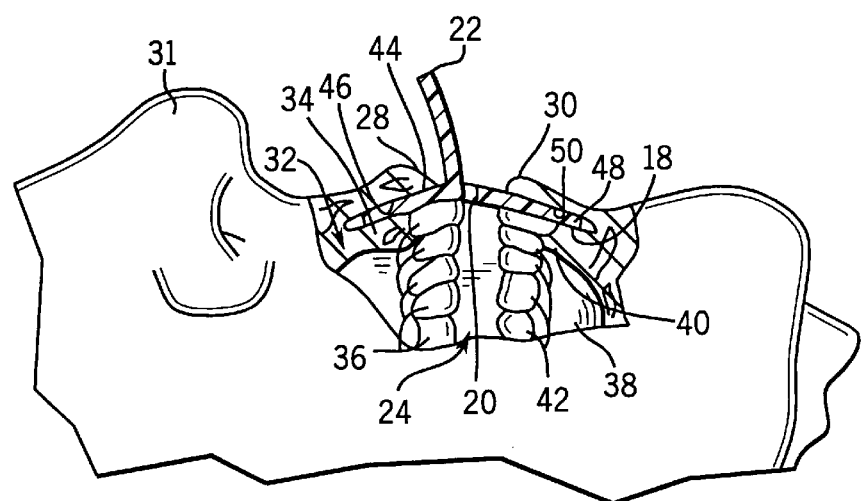
FIG. 4 is a side elevational view, partially in section, showing the device of FIG. 1 received in a user's mouth.

Oval plate 12 further includes opposing sides 16 and 18, FIG. 4 and a generally oval air passage 20 extending completely therethrough. Air passage 20 is centered in oval plate 12 to allow the passage of air into and out of a mouth 24 of a user 26, as hereinafter described. An alignment tab 22 extends from a first side 16 of oval plate 12, and is positioned adjacent air passage 20. Alignment tab 22 facilitates the handling of the snore prevention device by allowing the user 26 to grasp the alignment tab 22 when positioning snore prevention device 10 in mouth 24.

Figure 2:
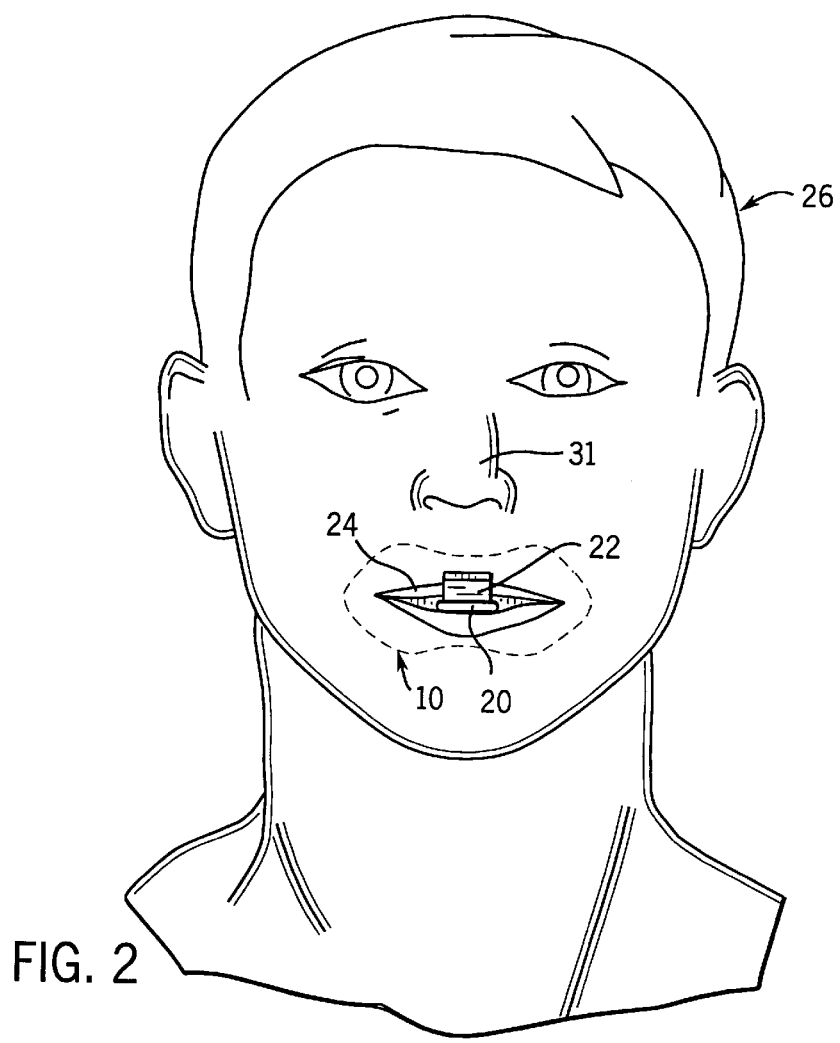
FIG. 2 is a front elevational view showing the device of FIG. 1 received in user's mouth.
Figure 3:
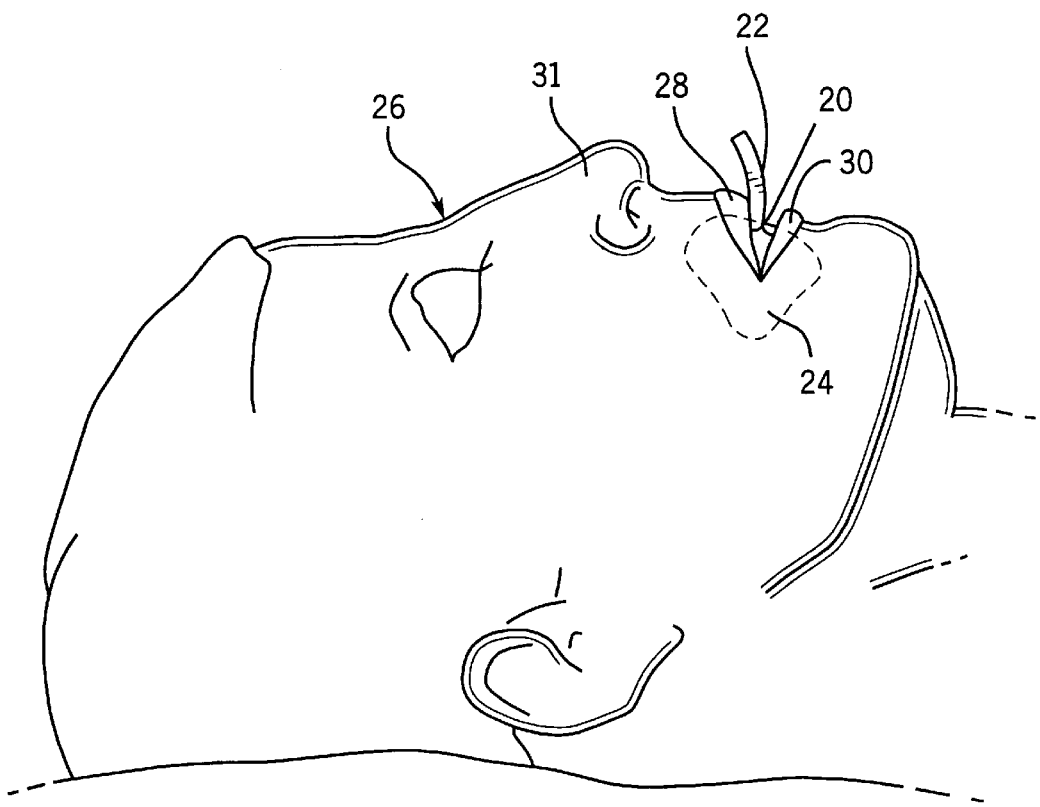
FIG. 3 is a side elevational view showing the device of FIG. 1 received in a user's mouth.

As best seen in FIGS. 2–4, snore prevention device 10 is designed for positioning in mouth 24 of a user 26 in order to prevent snoring. Mouth 24 includes a cavity which terminates externally at upper 28 and lower 30 lips, and internally at the pharynx or gullet. Mouth 24 encloses an upper mandible 32 having upper gums 34 and teeth 36 depending therefrom, and a lower mandible 38 likewise terminating at a lower gum 40 with lower teeth 42 extending upwardly therefrom.

In operation, user 26 grasps snore prevention device 10 by alignment tab 22, as previously described. As best seen in FIG. 4, snore prevention device 10 is inserted by user 26 into mouth 24 such that an upper portion 44 of oval plate 12 is positioned between the inner surface 46 of upper lip 28 and upper gum 34 and teeth 36 depending therefrom, and such that the lower portion 48 of oval plate 12 is positioned between the inner surface 50 of lower lip 30 and lower gum 40 and teeth 42 extending upwardly therefrom. As previously described, tapered edge 14 about the periphery of oval plate 12 is smooth, so as to not injure or cut inner surface 46 of lip 28, upper gum 34, inner surface 50 of lower lip 30, or lower gum 40.

When positioned in mouth 24 as described above, snore prevention device 10 allows the tongue of user 26 to move freely about in the cavity in mouth 24 to further increase the comfort level of user 26. In addition, movement of the tongue may facilitate the circulation of saliva in mouth 24 which may prevent the development of pyorrhea or the like.

The snore prevention device 10 is preferably molded from a pliable, plastic material which softens upon heating in hot water or other heating device, such as a microwave oven, but solidifies when cool. As a result, user 26 may heat the snore prevention device 10 such that it softens, and thereafter, position the oval plate 12 of the snore prevention device 10 in the user's mouth 24 as described above. In its softened state, oval plate 12 forms to the interior of mouth 24 so as to provide a more comfortable fit within the mouth 24 of user 26. The oval plate 12 of snore prevention device 10 may then be removed from mouth 24 in order to cool. As snore prevention device 10 cools, the pliable, plastic material from which it is constructed firms up, and thereafter retains a shape corresponding to its location in the interior of the mouth 24 of the user 26. This, in turn, renders snore prevention device 10 more comfortable for user 26 when oval plate 12 is received in mouth 24.

With oval plate 12 of snore prevention device 10 received within mouth 24 of user 26 as described above, alignment tab 22 abuts upper lip 28 of user 26 and aligns air passages behind the lower lip 30 of user 26. If user 26 maintains mouth 24 closed, the user 26 may breath normally through nose 31. On the other hand, if user 26 attempts to open mouth 24 to breath therethrough, upper 28 and lower 30 lips separate thereby exposing air passage 20 in oval plate 12 so as to allow the ingress and egress of air through air passage 20.

As is known, snoring generally occurs while the mouth is open, and breathing is done through the mouth. The passage of air through the mouth-causes a vibration or fluttering of the uvula, or soft palate, and of the diaphragm, which, in turn, causes the sound known as snoring.

With snore prevention device 10 in position, the air passage 20 in oval plate 12 reduces the amount and the velocity of air passing into the mouth 24 of user 26. The reduction in the amount and velocity of air passing through mouth 24 of user 26 reduces the vibration of the uvula, which causes the snoring sound. It is within the scope of the present invention to vary the dimension of air passage 20 so as to either increase or decrease the flow of air through the mouth. As a result, the snore prevention device 10 may be customized to allow the user 26 to breath comfortably with snore prevention device 10 positioned in mouth 24, and yet, still prevent vibration of the uvula.

Figure 5:
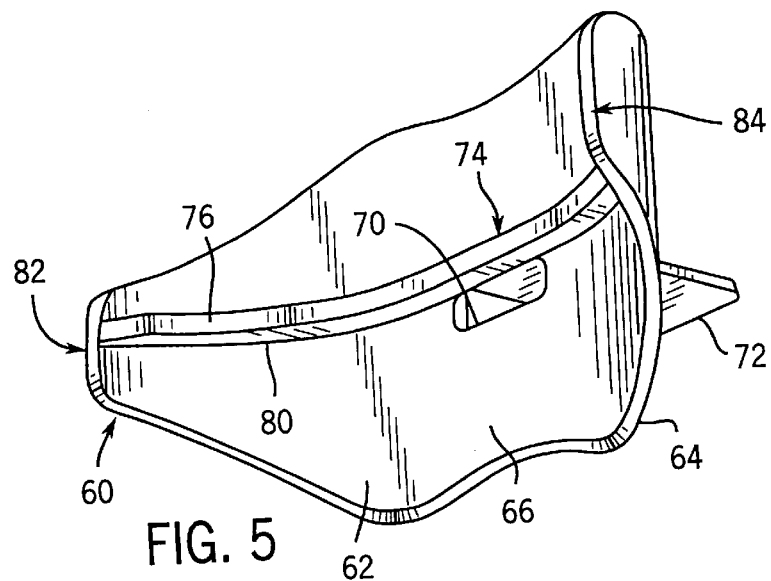
FIG. 5 is an isometric view of a snore and teeth grinding prevention device in accordance with the present invention.
Figure 6:
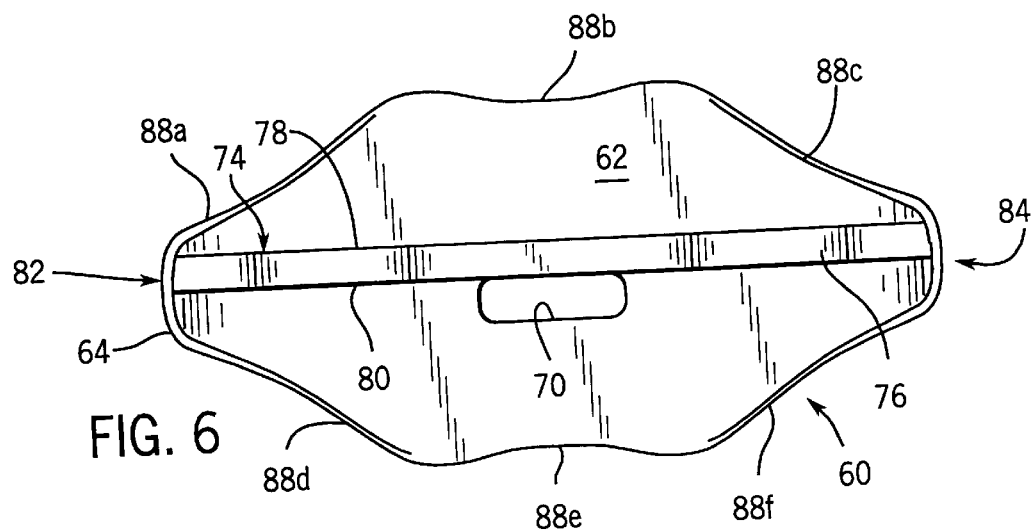
FIG. 6 is a rear elevational view of the device of FIG. 5.

Referring to FIG. 5, a snore and teeth grinding prevention device in accordance with the present invention is generally designated by the reference numeral 60. The snore and teeth grinding prevention device 60 includes a generally oval plate 62 having a tapered edge 64 which extends about the outer periphery of oval plate 62 and prevents the cutting of the interior of the user's mouth when device 60 is received therein.

Figure 7:
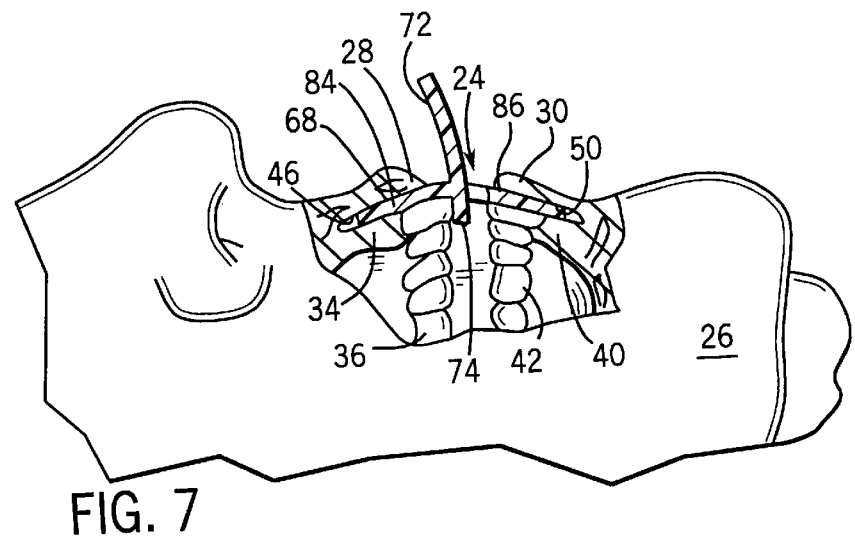
FIG. 7 is a side elevational view, partially in section, showing the device of FIG. 5 received in the user's mouth.

Oval plate 62 further includes opposing sides 66 and 68, FIG. 7, and a generally oval air passage 70 extending therethrough. Air passage 70 is centered in oval plate 62 to allow the passage of air into and out of mouth 24 of user 26. An alignment tab 72 extends from second side 68 of oval plate 62, and is positioned adjacent air passage 70. Alignment tab 72 facilitates the handling of the snore and teeth grinding prevention device by allowing user 26 to grasp the alignment tab 72 and positioning the snore and teeth grinding prevention device 10 in mouth 24.

A rib 74 extends along first side 66 of oval plate 12 and at a location adjacent opening 70. Rib 74 has a first inner edge 76 which separates upper and lower teeth engaging surfaces 78 and 80, respectively. As best seen in FIG. 5, the width of teeth engaging surfaces 78 and 80, and hence rib 74, is at a minimum adjacent air passage 70 and increases as rib 74 extends towards each end 82 and 84.

As best seen in FIG. 7, snore and teeth grinding prevention device 60 is designed for positioning in mouth 24 of a user 26 in order to prevent snoring and in order to prevent the grinding of teeth 36 and 42. In operation, user 26 grasps snore and teeth grinding prevention device 60 by alignment tab 72. Snore and teeth grinding prevention device 60 is inserted by user 26 in mouth 24 such that an upper portion 85 of oval plate 62 is positioned between the inner surface 46 of upper lip 28, and upper gum 34 and teeth 36 depending therefrom, and such that lower portion 86 of oval plate 62 is positioned between the inner surface 50 of lower lip 30, and lower gum 40 and teeth 42 extending upwardly therefrom. Tapered edge 64 about the periphery of oval plate 62 is smooth so as not to injure or cut inner surface 46 of lip 28, upper gum 34, inner surface 50 of lower lip 34, or lower gum 40. In addition, a plurality of concave cutouts 88a–f may be provided in the outer periphery of the oval plate 62 in order that oval plate 62 fits more comfortably in the mouth of user 26.

As the snore and teeth grinding prevention device 60 is positioned in mouth 24 of user 26, rib 74 is positioned between teeth 36 depending from upper gum 34 and teeth 42 extending from lower gum 40. As best seen in FIG. 7, rib 74 provides a barrier so as to prevent teeth 36 from engaging teeth 42 in order to prevent the grinding of teeth 36 against teeth 42 during sleep. In order to accommodate teeth of different widths, the width of rib 74 increases as it extends from the interior of oval plate 62 towards ends 82 and 84, as previously described. Since teeth in the rear of the mouth 24, i.e. molars, are wider than the teeth at the front of mouth 24, the width of rib 74, corresponding increases at ends 82 and 84 of oval plate 62 in order to prevent engagement of the molars during sleep.

When positioned in mouth 24, as described above, the snore and teeth grinding prevention device 60 allows the tongue of user 26 to move freely about in the cavity in mouth 24 to further increase the comfort level of user 26. In addition, movement of the tongue facilitates the circulation of the saliva in mouth 24 which may prevent the development of pyorrhea or the like.

As with respect to snore prevention device 10, snore and teeth grinding prevention device 60 is preferably molded from a pliable, plastic material which softens upon heating in hot water or other heating device, such as a microwave oven, but solidifies when cool. In use, user 26 heats the snore and teeth grinding prevention device 60 such that it softens. Thereafter, the user 26 positions the oval plate 62 of the snore and teeth grinding prevention device 60 in their mouth 26 as described above. In its soften state, oval plate 62 forms to the interior of mouth 24 so as to provide a more comfortable fit within the mouth 24 of user 26. The oval plate 62 of the snore and teeth grinding prevention device 60 may then be removed from mouth 24 in order to cool. As snore and teeth grinding prevention device 60 cools, the pliable, plastic material firms up, and thereafter retains its shape corresponding to its location in the interior of the mouth 24 of the user 26.

It can be seen from the above description that various modes of carrying out the invention are contemplated as being within the scope of the following claims particularly pointing out and distinctly claiming the subject matter regarded as the invention.

I claim:

1. A device for placement in the mouth of a user, the mouth having an exterior portion terminating in upper and lower lips, a posterior portion, and upper and lower gums therebetween each gum, having teeth extending therefrom, comprising:

a generally oval plate for receipt in the mouth between the teeth and the lips, the plate including an aperture centered therein for accommodating airflow into and out of the mouth;

a tab member extending lateral from a first side of the oval plate, the tab member immediately adjacent the aperture such that when the oval plate is received in the mouth and the upper and lower lips are separated, the tab member locates the aperture to allow for the flow of air into and out of the mouth therethrough; and a rib extending along a second side of the oval plate such that when the oval plate is received in the mouth, the rib is positioned between the teeth extending from the upper gum and the teeth extending from the lower gum wherein the rib has a first predetermined width at the location adjacent the aperture and wherein the width of the rib increases as the rib extends toward the ends of the oval plate.

2. The device of claim 1 wherein the oval plate has first and second ends and the rib extends along the second side of the oval plate therebetween, the rib having a width.

3. The device of claim 1 wherein the generally oval plate includes a tapered, outer edge for preventing abrasions in the mouth.

4. The device of claim 1 wherein the generally oval plate is constructed from a plastic material which softens and becomes pliable during heating to allow an impression of a portion of the interior of the mouth to be made, and which upon cooling retains the impressed shape.

5. The device of claim 1 wherein the tab member and the generally oval plate are integrally molded.

6. A device for placement in a human mouth having upper and lower gums therein and terminating at a pair of lips, each gum having teeth extending therefrom, comprising:

a contoured, generally elliptical plate for receipt in a mouth between the gums and the lips, the plate including an air passage therethrough and having first and second ends and first and second opposing sides;

means connected to the plate for positioning the air passage in the mouth and for allowing the continuous ingress and egress of air through the air passage when the lips are separated; and means for preventing the teeth extending from the upper gum from engaging the teeth extending from the lower gum, the preventing means including a rib extending along the second side of the plate between the first and second ends of the generally elliptical plate such that a portion of the rib is adjacent the air passage through the generally elliptical plate, and such that when the oval plate is received in the mouth, the rib is positioned between the teeth extending from the upper gum and the teeth extending from the lower gum, wherein the rib has a first predetermined width at a location adjacent the air passage through the general elliptical plate, and a second greater width at a location adjacent the first end of the generally elliptical plate.

7. The device of claim 6 wherein the means for positioning the air passage includes a tab member extending laterally from a first side of the plate, the tab member protruding between the lips when the tab member is positioned in the mouth.

8. The device of claim 7 wherein the tab member is immediately adjacent the air passage.

9. The device of claim 6 wherein the generally elliptical plate includes a tapered, outer edge for preventing abrasions in the mouth.

10. The device of claim 6 wherein the generally elliptical plate is constructed from a plastic material which softens and becomes pliable during heating to allow an impression of a portion of the interior of the mouth to be made, and which upon cooling retains the impressed shape.

11. The device of claim 6 wherein the tab member and the generally elliptical plate are integrally molded.

12. A device for placement in the mouth of a user, the mouth having an exterior portion terminating in upper and lower lips, a posterior portion, and upper and lower gums therebetween each gum, having teeth extending therefrom, comprising:

a generally oval plate for receipt in the mouth between the teeth and the lips, the plate including an aperture centered therein for accommodating airflow into and out of the mouth;

a tab member extending laterally from a first side of the oval plate, the tab member immediately adjacent the aperture such that when the oval plate is received in the mouth and the upper and lower lips are separated, the tab member locates the aperture to allow for the flow of air into and out of the mouth therethrough; and a rib extending along at least a portion of a second side of the oval plate, such that when the oval plate is received in the mouth, the rib is positioned between the teeth extending from the upper gum, wherein the rib has a first width at a first location and a second width greater than the first width at a second location near the ends of the oval plate and the teeth extending from the lower gum.

13. The device of claim 12 wherein the oval plate has first and second ends and the rib extends along the second side of the oval plate therebetween, the rib having a width.

14. The device of claim 12 wherein the generally oval plate includes a tapered, outer edge for preventing abrasions in the mouth.

15. The device of claim 12 wherein the generally oval plate is constructed from a plastic material which softens and becomes pliable during heating to allow an impression of a portion of the interior of the mouth to be made, and which upon cooling retains the impressed shape.

16. The device of claim 12 wherein the tab member and the generally oval plate are integrally molded.

17. A device for placement in a human mouth having upper and lower gums therein and terminating at a pair of lips, each gum having teeth extending therefrom, comprising:
   a generally elliptical plate for receipt in a mouth between the gums and the lips, the plate having first and second ends and including an air passage therethrough;
   positioning structure connected to the plate for positioning the air passage in the mouth and for allowing the continuous ingress and egress of air through the air passage when the lips are separated; and
   a rib extending along at least a second portion of a second side of the oval plate such that when the oval plate is received in the mouth, the rib is positioned between the teeth extending from the upper gum wherein the rib has a first width at a first location and a second width greater than the first width at a second location near the ends of the oval plate and the teeth extending from the lower gum.

18. The device of claim 17 wherein the positioning structure includes a tab member extending laterally from a first side of the plate, the tab member protruding between the lips when the plate is positioned in the mouth.

19. The device of claim 18 wherein the tab member is immediately adjacent the air passage.

20. The device of claim 18 wherein the tab member and the generally elliptical plate are integrally molded.

21. The device of claim 17 wherein the generally elliptical plate includes a tapered, outer edge for preventing abrasions in the mouth.

22. The device of claim 17 wherein the generally elliptical plate is constructed from a plastic material which softens and becomes pliable during heating to allow an impression of a portion of the interior of the mouth to be made, and which upon cooling retains the impressed shape.

23. The device of claim 17 wherein the rib extends between the first and second ends of the generally elliptical plate.

24. The device of claim 23 wherein a portion of the rib is adjacent the air passage through the generally elliptical plate.

25. The device of claim 24 wherein the rib has a first predetermined width at a location adjacent the air passage through the general elliptical plate, and a second greater width at a location adjacent the first end of the generally elliptical plate.

* * * * *